United States Patent
Clark et al.

(10) Patent No.: US 8,871,158 B2
(45) Date of Patent: Oct. 28, 2014

(54) HISTOLOGY SLIDE AND PARAFFIN BLOCK SYSTEM

(71) Applicants: H. Lee Moffitt Cancer Center and Research Institute, Inc., Tampa, FL (US); Evergreen Industries, Inc., Los Angeles, CA (US)

(72) Inventors: Noel D. Clark, Riverview, FL (US); Johnson Wong, Rolling Hills, CA (US)

(73) Assignee: H. Lee Moffitt Cancer Center and Research Institute, Inc., Tamp, FL (US)

( * ) Notice: Subject to any disclaimer, the term of this patent is extended or adjusted under 35 U.S.C. 154(b) by 0 days.

(21) Appl. No.: 14/072,104

(22) Filed: Nov. 5, 2013

(65) Prior Publication Data

US 2014/0134080 A1    May 15, 2014

Related U.S. Application Data

(63) Continuation of application No. PCT/US2012/036773, filed on May 7, 2012.

(60) Provisional application No. 61/482,895, filed on May 5, 2011.

(51) Int. Cl.
*A61B 10/00* (2006.01)
*A01N 1/02* (2006.01)
*G01N 1/36* (2006.01)

(52) U.S. Cl.
CPC ............... *A01N 1/0273* (2013.01); *G01N 1/36* (2013.01)
USPC .................. 422/536; 422/63; 422/64; 422/65; 422/66; 422/67; 436/180

(58) Field of Classification Search
USPC ............................... 422/63–67, 536; 436/180
See application file for complete search history.

(56) References Cited

U.S. PATENT DOCUMENTS

| | | | |
|---|---|---|---|
| 2,996,762 A | 8/1961 | McCormick |
| 3,733,768 A | 5/1973 | Carls et al. |
| 3,996,326 A | 12/1976 | Schachet |
| 5,626,630 A | 5/1997 | Markowitz |
| 5,855,609 A | 1/1999 | Knapp |
| 5,983,467 A | 11/1999 | Duffy |
| 7,780,919 B2 | 8/2010 | McCormick |

FOREIGN PATENT DOCUMENTS

| | | |
|---|---|---|
| JP | 09-145571 A | 6/1997 |
| JP | 2007-255896 A | 10/2007 |

OTHER PUBLICATIONS

International Search Report and Written Opinion of the International Searching Authority issued on Nov. 28, 2012 for International Patent Application No. PCT/US2012/036773.

*Primary Examiner* — Jyoti Nagpaul
(74) *Attorney, Agent, or Firm* — Robert J. Varkonyi; Smith & Hopen, P.A.

(57) ABSTRACT

A protective sheath for prolonged storage of pathology paraffin blocks. The sheath protects the paraffin block against gouging, scratching, denting, rodents, and insects. A pathology slide slides into a slot in the protective sheath and is held into place by retainers running on the interior face of the protective sheath. A paraffin block cassette accepts a paraffin block and slides into a sample block sleeve holder disposed on one edge of the sheath.

15 Claims, 14 Drawing Sheets

HISTOLOGY SLIDE AND PARAFFIN BLOCK SYSTEM

CROSS REFERENCE TO RELATED APPLICATION

This application is a continuation of prior filed International Application No. PCT/US2012/036773 filed on May 7, 2012, which claims priority to U.S. Provisional Patent Application No. 61/482,895, entitled "Histology Slide and Paraffin Block Storage System", filed on May 5, 2011, the contents of which are herein incorporated by reference.

FIELD OF THE INVENTION

The invention related to histology sample storage. Specifically, the invention is a protective sleeve for stored paraffin blocks and histology slides.

BACKGROUND OF THE INVENTION

Each day, tens of thousands of patients go through inpatient and outpatient procedures resulting in either biopsies or excised tissues. These biological samples are often used for diagnostic evaluation to determine the present of disease and to determine the appropriate treatment for the disease or research. Tissue samples obtained from a patient for molecular diagnostic and analysis, such as RNA, DNA, and protein analysis, which have become commonplace in research for the treatment of disease require quality, intact nucleic acids.

A biopsy sample or tissue is typically sectioned using cryostatic sections, as is known in the art, or processed and embedded in paraffin blocks to facilitate cutting of pathological slides used in diagnostic and research applications. In order to facilitate visualizing these biopsies by microscopic examination, the cells/tissue must first be processed and embedded in a carrier medium to allow cutting after paraffin embedding. After the specimen has been collected, the tissue sample is preserved by passing it through fixatives to remove water from the sample, and then processed with a solvent to dissolve fatty materials and "clear" the tissue sample. After being "cleared", the tissue sample is placed in molten paraffin and it is infiltrated with the wax, which replaces the solvent which will evaporate or be diluted to trace levels, causing all the tissue to be infiltrated with a common wax binder. The sample may then be cut in a section plane to be presented to the microtome blade for creation of a microscope slide, which may be examined microscopically for information collection. The paraffin wax capsules which form the specimen samples are cast is small containers called "boats", or in two-piece containers such as those described in McCormick (U.S. Pat. No. 2,996,762). A microtome is used to section the embedded tissue, which are mounted on a substrate, like a histology slide, for staining or further analysis, and subsequent histological characterization. The remainder of the embedded tissue specimen is stored for future use and reference.

A variety of automated systems have been developed for use in histology laboratories for labeling slides prior to mounting specimens to the slides. Many of the systems focus on labeling the slide with specific information, such as patient information and tissue type or a printed bar code which may be scanned to obtain the patient database records. For example, Carls, et al. (U.S. Pat. No. 3,733,768) describes a histology specimen tray with rows of compartments for storing specimens using wax to fix the specimens into place.

These blocks and slides are soon thereafter manually filed and archived into one of several plastic, metal, or cardboard filing/storage systems. As a general rule of policy and law, the blocks and slides are retained for as many as 10 years or longer. Systems are known that permit processing of tissue samples, such as those described in McCormick (U.S. application Ser. No. 12/425,583). During this filing process the blocks, which have a wax/paraffin media can be damaged. The blocks can be scratched, gouged, dislodged from the parent cassette, or even melted, if the temperature of the storage location is too hot. In addition, other hazards of storage may arise with long-term conditions. These may include, but are not limited to, insect damage, rodent threat and damage, and dirt and debris in the storage location.

Later, when the block is needed for additional staining or review purposes, the block will be handled again and subjected to the same handling/storage conditions. Normally, the administrative person pulling the block will leave a tag indicating that the block has been removed and for whom the block was pulled (the requesting pathologist's name). This is supposed to give a tracking aspect to the storage system. However, as human nature would allow, this seldom is achieved and blocks go unaccounted for and then time is wasted tracking down the person or office which now possesses the block. In addition, current storage systems tightly store the histology sample paraffin blocks, to save on storage space. As a consequence of this tight fit, if the person does place a "pulled" tag in the area, most of the time the tag gets pulled away by constant opening and closing of the tray/drawer. The same holds true for the pathology slides which were created from the parent block.

Therefore, the art is underdeveloped for long-term paraffin block storage which allows easy identification of the sample, sample location, and safe storage conditions.

SUMMARY OF THE INVENTION

A protective sheath is provided to both protect the histology sample and slide, and to reduce or eliminate loss of the sample and slide. The sheath includes a histology slide protective member and histology sample protective member permanently connected together. The histology slide protective member is formed of four vertical walls disposed in communication with a lower horizontal wall, such that the walls define an open-faced box with an internal space. This interior space is dimensioned to accept at least one histology slide. A plurality of ridges are disposed on the interior horizontal walls and adapted to accept the histology slide. For example, the ridge may be four ridges disposed on the interior horizontal walls or eight ridges for accepting two histology slides. Where eight ridges are used, four of the ridges are disposed on the interior horizontal walls of the histology slide protective member forming a first set of slide ridges and a second set of slide ridges. Two additional ridges are disposed between the first set of slide ridges and two additional ridges are disposed between the second set of slide ridges, such that the eight ridges are adapted to accept two histology slides in the histology slide member.

The histology sample protective member comprises a sample block sleeve holder disposed on a first vertical wall of the histology slide protective member and formed of a first sample member vertical wall and third sample member vertical wall connected to first vertical wall of the histology slide protective member, and a second sample member vertical wall connected to the first sample member vertical wall and third sample member vertical wall, such that the sample member vertical walls and horizontal wall define an interstitial space adapted to accept a sample block sleeve. Optionally, the histology sample protective member comprises includes a plurality of ridges disposed on the interior horizontal walls of the first sample member vertical wall and third sample member vertical wall and adapted to accept the sample block sleeve. The ridges may be designed to tightly hold the sample block sleeve to prevent movement in the histology sample protective member. The histology sample protective member includes a sample block sleeve having three vertical sample block sleeve walls disposed in communication with an upper horizontal sample block sleeve wall and a lower horizontal sample block sleeve wall. The walls define an open-faced box, having an internal sample/paraffin block space that is adapted to accept a sample or paraffin block.

The horizontal walls of the histology slide protective member and histology sample protective member may be two independent horizontal walls or may be integrated into one horizontal wall. Further, the protective sheath may include means to secure the sample block sleeve. Examples include clips, buckle or clasp, flange, or strap to lock the slide or slides into place and/or the sample block sleeve. For example clips may be disposed on the upper edges of the walls of the sheath and extend into the interior space, adjacent to the slide or sample block sleeve. Upon insertion of the slide or sample block sleeve into the sheath, the clip moves into a locked position, by for example springs, securing the slide or sample block sleeve into the sheath. Alternatively, velcro or a "slidingly engaging fastener" (Duffy, U.S. Pat. No. 5,983,467) may be used to reversibly fix the slide or sample block sleeve to the sheath. For example, a strip of velcro may be adhered to the bottom edge of a slide, with a corresponding section of velcro adhered to the bottom wall of the sheath. Upon insertion of the slide into the sheath, the two velcro sections grasp, securing the slide to the sheath. The sheath optionally also includes a horizontal retrieval lip disposed on the upper edge of a second vertical wall of the histology slide protective. The lip facilitates retrieval of the sheath from a storage location. Additionally, the sheath may also include a retrieval clip disposed on the retrieval lip, further facilitating retrieval or permitting automated retrieval of the sheath. The sheath optionally includes a retention system, such as a pivoting lid, slidingly connected lid, or pressure-fitted lid.

The pivoting lid includes a lid face dimensioned to cover the upper edge of the histology slide protective member and histology sample protective member. A plurality of lid hinge faces disposed perpendicular to the adapted to the lid face engage a plurality of hinge points. The hinge points are disposed on a second vertical wall of the histology slide protective member and a third vertical wall of the histology slide protective member, or on a plurality of hinge projections. Where the hinge projection is used, the projection is disposed adjacent to and parallel the second vertical wall of the histology slide protective member and the third vertical wall of the histology slide protective member. Optionally, the pivoting lid also includes a lip on the lid face. The lip runs along the first front sample block sleeve edge, second side sample block edge, third side sample block edge, first front slide storage edge, second side slide storage edge, and third side slide storage edge. The lid hinge faces are disposed on the second side slide storage edge and the third side slide storage edge, and may optionally be incorporated into the lip, as it runs along the second side slide storage edge and the third side slide storage edge. The lid also optionally includes a spring-loaded clip or pressure loaded clip disposed on the lip, wherein the spring-loaded clip or pressure loaded clip is disposed on the first front sample block sleeve edge. Where the clip is used, a clip lock disposed on the face of the first sample member vertical wall, and wherein the clip lock is adapted to accept the spring-loaded clip or pressure loaded clip.

The slidingly connected lid includes a at least one channel disposed on the interior face of the first vertical wall of the histology slide protective member, the second vertical wall of the histology slide protective member, the third vertical wall of the histology slide protective member, the first sample member vertical wall, the second sample member vertical wall, and the third sample member vertical wall in communication with the first vertical wall of the histology slide protective member. The sliding lid is adapted to engage the channel and dimensioned to cover the upper edge of the histology slide protective member and histology sample protective member. Optionally, the lid includes an elevated lip, wherein the wherein the first vertical wall of the histology slide protective member, the second vertical wall of the histology slide protective member, the third vertical wall of the histology slide protective member, the first sample member vertical wall, the second sample member vertical wall, and the third sample member vertical wall in communication with the first vertical wall of the histology slide protective member are elongated to form the elevated lip. The lid may also optionally include a spring-loaded clip or pressure loaded clip. Where the a spring-loaded clip or pressure loaded clip is disposed on the back edge of the sliding lid, a lid lock groove is disposed on the sheath retrieval lip and adapted to engage the spring-loaded clip, wherein the sheath retrieval lip is disposed on the upper edge of a second vertical wall of the histology slide protective member.

The pressure-fitted lid includes an elevated lip, wherein the first vertical wall of the histology slide protective member, the second vertical wall of the histology slide protective member, the third vertical wall of the histology slide protective member, fourth vertical wall of the histology slide protective member, the first sample member vertical wall, the second sample member vertical wall, and the third sample member vertical wall in communication with the first vertical wall of the histology slide protective member are elongated to form the elevated lip. A friction lid, dimensioned to fit the elevated lip is adapted to frictionly engage the interior space of the elevated lip. A textured or friction material is optionally disposed on the interior face of elevated lip, where the textured or friction material is adapted to engage the pressure-fitted lid. Exemplary textured or friction materials include ridges disposed in the interior face of the elevated lip, sand or other abrasive materials integrated into the interior face of the elevated lip, and felt or other textile material.

The sheath may be made of any material known in the art. Some examples include plastics such as polyethylene, polypropylene, polyethylene terephthalate, polyvinylchloride, polyvinylidenechloride, polycarbonate, polyurethane, polyamide, polytetrafluoroethylene, polyvinylacetate, wood, ceramic, cellulose materials such as cardboard, fiberboard, metal such as titanium, stainless steel, and surgical steel. Specific embodiments are envisioned constructed of plastic. Other useful plastics include acrylonitrile butadiene styrene (ABS), high impact polystyrene (HIPS), acrylic (PMMA), cellulose acetate, cyclic olefin copolymer (COC), ethylene-vinyl acetate (EVA), ethylene vinyl alcohol (EVOH), polyvinylfluoride (PVF), polyvinylidene fluoride (PVDF), polytetrafluoroethylene (PTFE), polychlorotrifluoroethylene (PCTFE), fluorinated ethylene-propylene (FEP), perfluoroalkoxy polymer (PFA), polyethylenechlorotrifluoroethylene (ECTFE), polyethylenetetrafluoroethylene (ETFE), perfluoropolyether (PCPE), acrylic/PVC polymer, aromatic polyester polymers (liquid crystal polymer), polyoxymethylene (acetal), polyamide (PA, nylon), polyamide-imide (PAI), polyaryletherketone (PAEK), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoate (PHA), polyketone (PK), polyester, polyethylene (PE), polyetheretherketone (PEEK), polyetherimide (PEI), polyethersulfone (PES), chlorinated polyethylene (CPE), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC), styrene-acrylonitrile (SAN).

The protective sheath may be formed by any suitable means known in the art. For example, where the sheath is made from a polymer material, the sheath may be formed using a mold with the polymer applied to the mold under appropriate heat and pressure to allow curing of the polymer. Other means of forming the sheath using polymers and resins includes extrusion molding, vacuum forming, thermoforming, and injection molding. Metals and cellulose materials may be formed using a die or compression molded.

Identification means may be included on the sheath, such as bar code, medical information transponder, such as those described by Knapp (U.S. Pat. No. 5,855,609) and Markowitz, et al. (U.S. Pat. No. 5,626,630), or patient code or information. The identification is optionally included on the side of the sheath, allowing a plurality of sheaths to be stored side-by-side, while concurrently providing easy identification of the patient or histology information of the sample contained in the sheath.

In some embodiments, the edges of the at least one tissue slide opening are coated with a compound, such as Teflon, polyester, para-phenylenediamine, terephthaloyl chloride polymer, carbon fiber, expanded PTFE, meta-phenylenediamine, nylon, polypropylene, latex, silicone, polyurethane, polyisoproprene polyvinylchloride, ethylene propylene diene monomer, styrene, cornstarch powder, graphite, meta-aramid compounds, or para-aramid compounds.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

As used herein, "about" means approximately or nearly and in the context of a numerical value or range set forth means±15% of the numerical.

Figure 1:
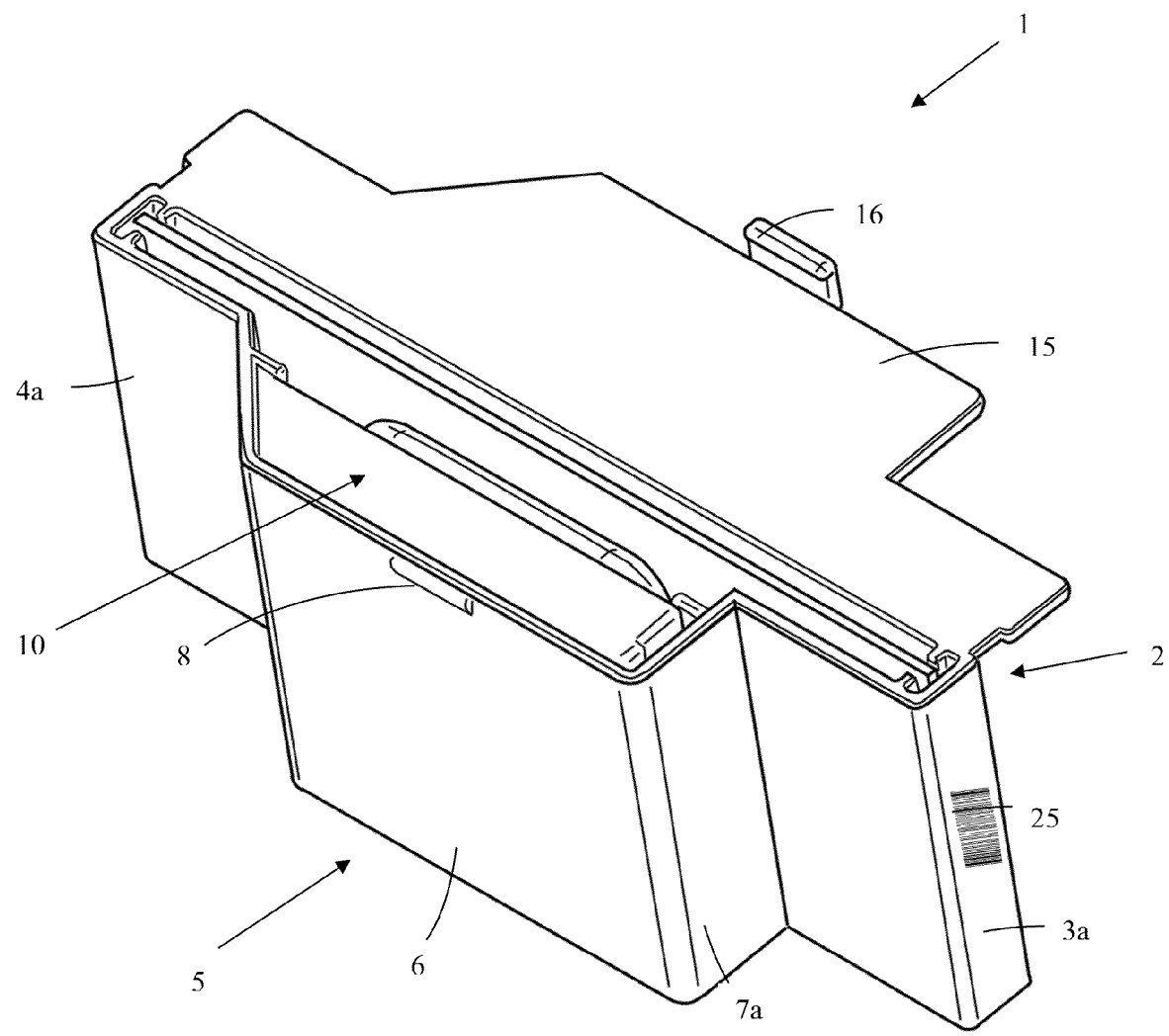
FIG. 1 is an isometric view of the inventive sheath, showing a histology slide placed in the slide retainer and a sample block sleeve.

As used herein, "front", "back", "upper" and "lower" or "bottom" are referenced based on the image depicted in FIG. 1. "Front" means any portion of the sheath directed to the bottom left in FIG. 1. For example, reference number 6 is the front-most portion of the sheath. "Back" is any portion of the sheath directed opposite to the front, i.e. directed toward the upper right in FIG. 1. "Upper" is in a direction toward the top of FIG. 1, and "lower" or "bottom" is directed toward the bottom of FIG. 1.

As used herein "patient", means members of the animal kingdom, including mammals, such as but not limited to, primates including humans, gorillas and monkeys; rodents, such as mice, fish, reptiles and birds. The patient may be any animal requiring therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

As used herein "sample" or "biological sample" means a biological tissue or solid material taken from a patient.

As used herein, "substantially" means largely if not wholly that which is specified but so close that the difference is insignificant, and such differences do not influence the functional properties of the term beyond the normal tolerances permitted by one of skill in the art. In some embodiments, "substantially" means that the differences do not vary by more than 10% or less.

Example 1

Figure 4:
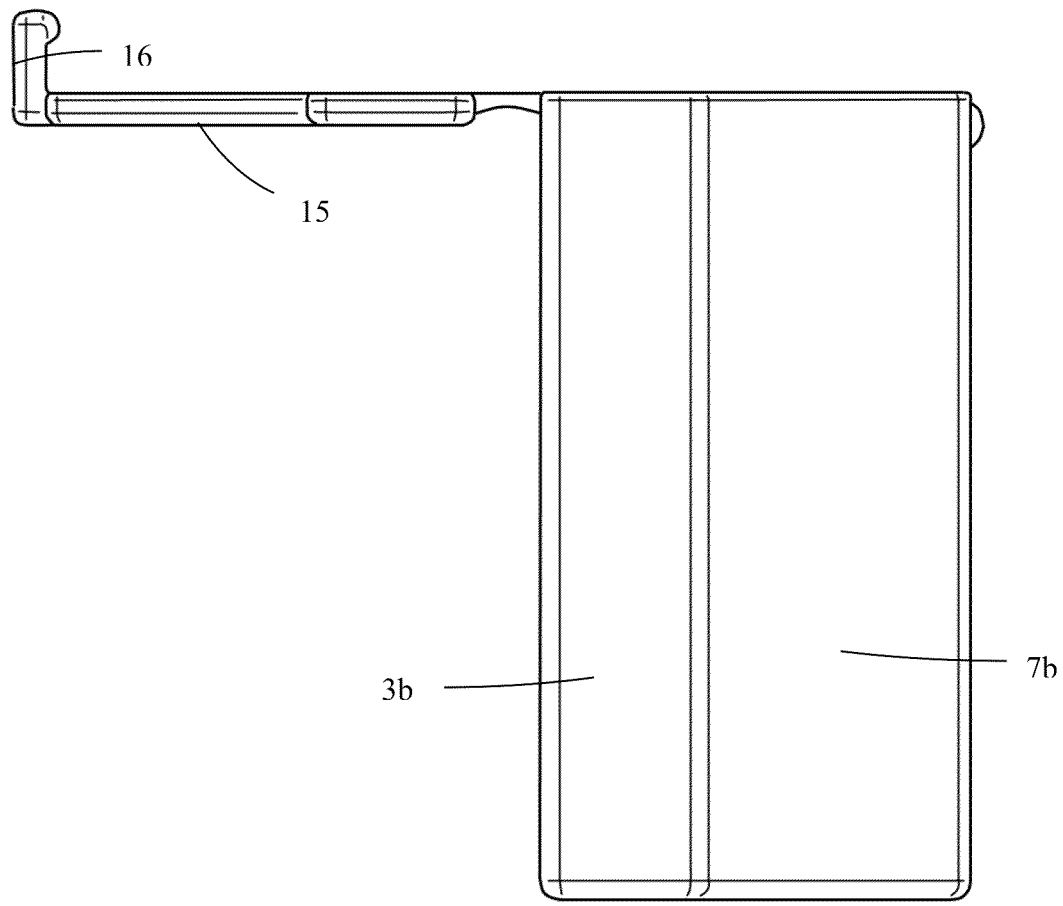
FIG. 4 is a side view of the inventive sheath.

Sheath 1 comprises slide protective member 2 and histology sample protective member 5, as seen in FIG. 1. Slide protective member 2 comprises first vertical slide storage side wall 3a, second slide storage side wall 3b, vertical slide storage front wall 4a, vertical slide storage back wall 4b, and horizontal sheath bottom wall 9, which form an "open box" and define an inner space in slide storage 2. Optional identifier 25 is disposed on first vertical body side wall 3a, vertical slide storage back wall 4b, or on sheath retrieval lip 15. Histology sample protective member 5 comprises first vertical sample block sleeve side wall 7a, second vertical sample block sleeve side wall 7b, vertical sample block sleeve front wall 6, and horizontal sheath bottom wall 9, which form an "open box" and define an inner space in histology sample protective member 5. Histology sample protective member 5 is typically wider than slide protective member 2, as seen in FIG. 4, and integrated into vertical slide storage front wall 4a, such that slide protective member 2 and histology sample protective member 5 form a single, integrated sheath 1. Optionally, sample protection member projection 8 is disposed on the exterior face of sample block sleeve front wall 6.

Figure 2:
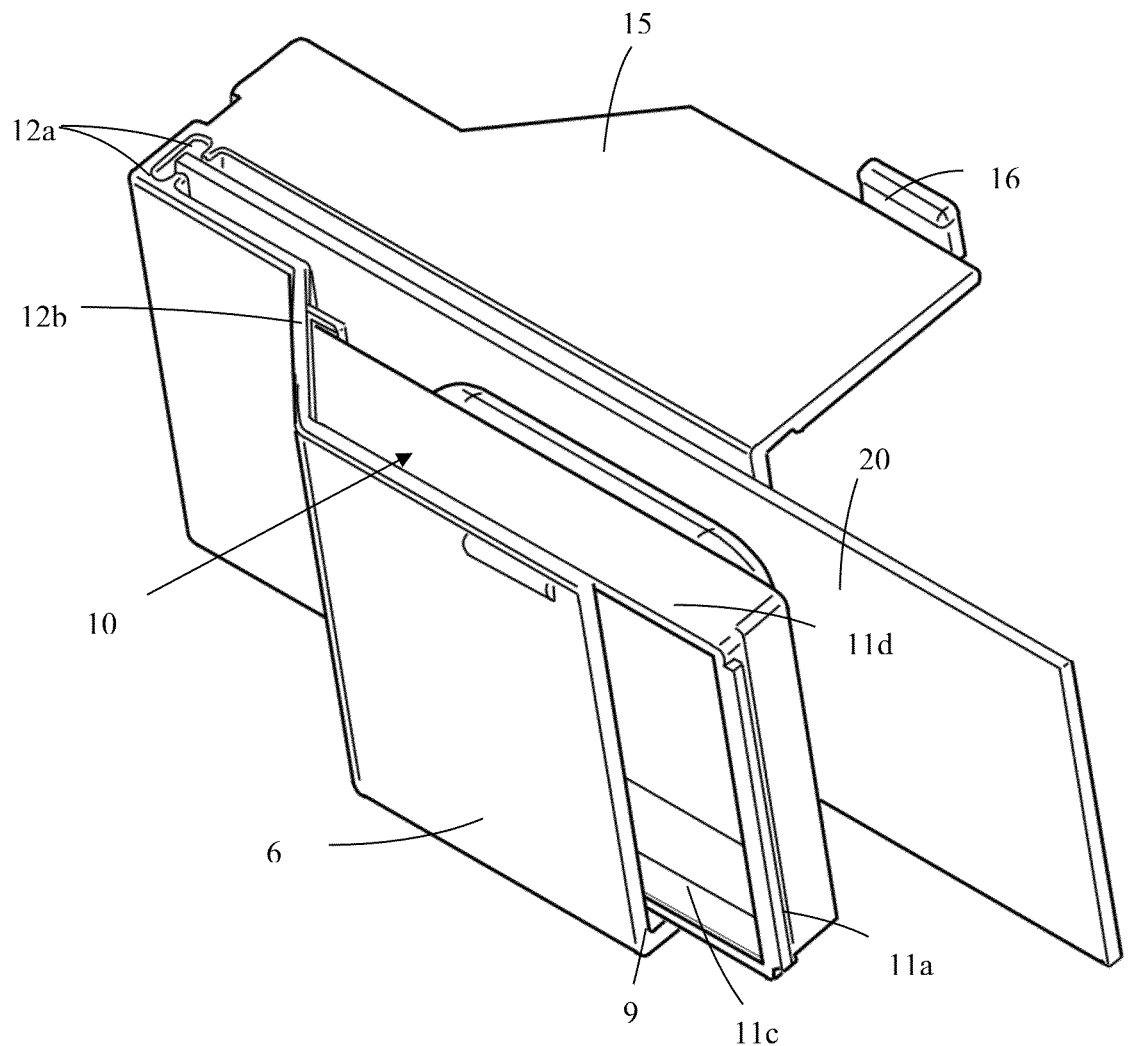
FIG. 2 is a cut-away isometric view of the inventive sheath, showing a histology slide placed in the slide retainer and an empty sample block sleeve.
Figure 3:
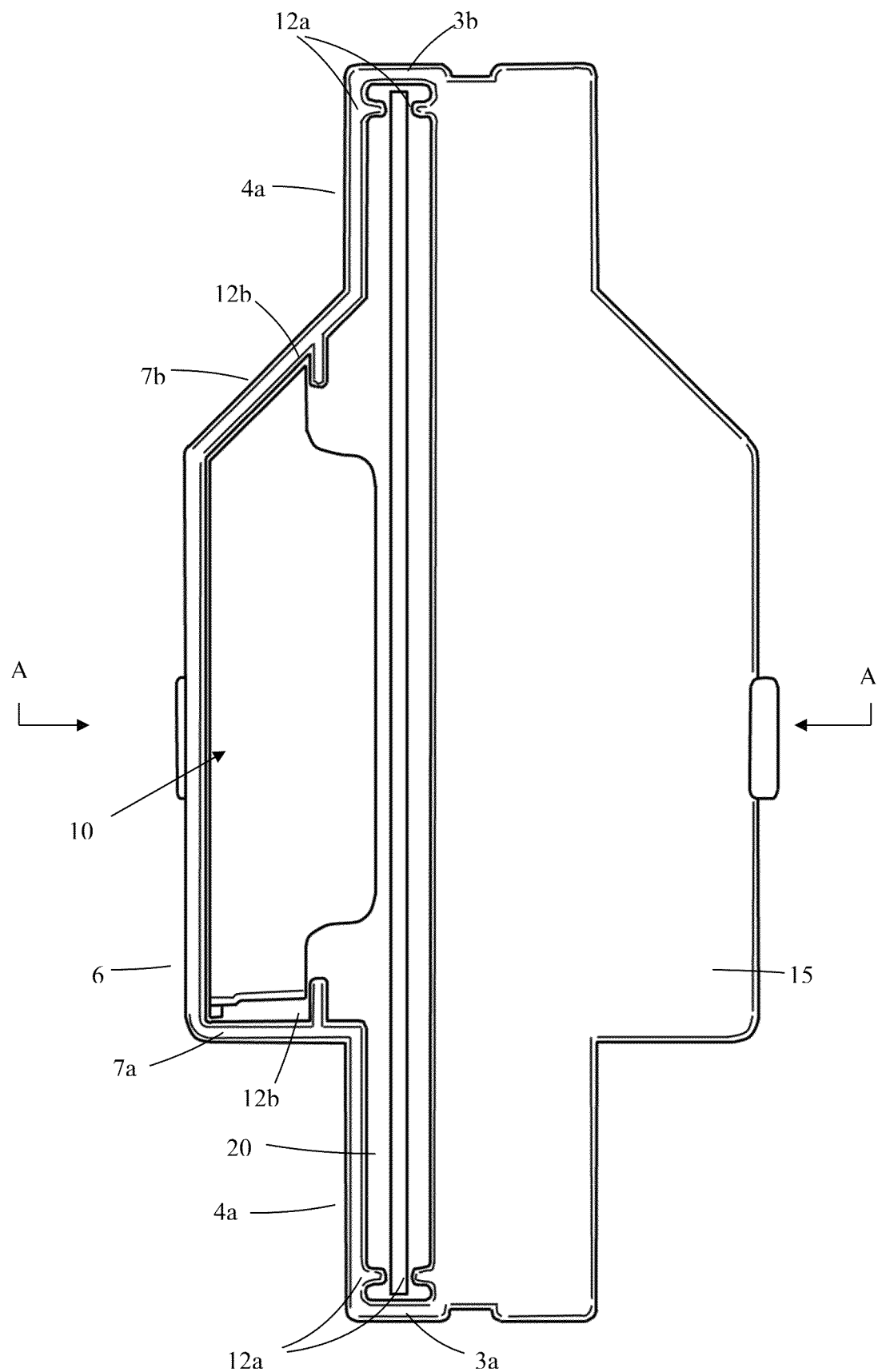
FIG. 3 is a top-down view of the inventive sheath, showing a histology slide placed in the slide retainer and a sample block sleeve.

A plurality of slide retainers 12a are integrated into the internal space in slide storage 2, as seen in FIGS. 2 and 3. Slide retainers 12a are disposed adjacent to the corners of the inner space of slide protective member, and are protrusions on the walls of vertical slide storage front wall 4a and vertical slide storage back wall 4b. In some embodiments, slide retainers 12a are knobs on the upper edge of vertical slide storage front wall 4a and vertical slide storage back wall 4b, such that the slide retainer only contacts the uppermost portion of slide 20. Conversely, slide retainers 12a run the length of the internal space in slide storage 2, from the upper edge of vertical slide storage front wall 4a and vertical slide storage back wall 4b to the bottom edge of the vertical walls, i.e. adjacent to the upper edge of sheath bottom wall 9. Slide retainers 12a are used to position slide 20 in the internal space of slide storage 2, and prevent slide 20 from contacting sample block sleeve 10. Sample block sleeve retainers 12b are integrated into sample block sleeve holder 5, and run from the upper edge of first vertical sample block sleeve side wall 7a and second vertical sample block sleeve side wall 7b to the bottom edge of the side walls, as seen in FIG. 3.

Sheath retrieval lip 15, is disposed adjacent to the upper edge of slide storage 2 and extends horizontally until it ends in sheath retrieval clip 16, as seen in FIGS. 3 and 4. Sheath retrieval lip 15 can be a mirror image shape of slide protective member 2 and histology sample protective member 5, as seen in the images, a rectangular lip, or any shape known to one skilled in the art.

Figure 6:
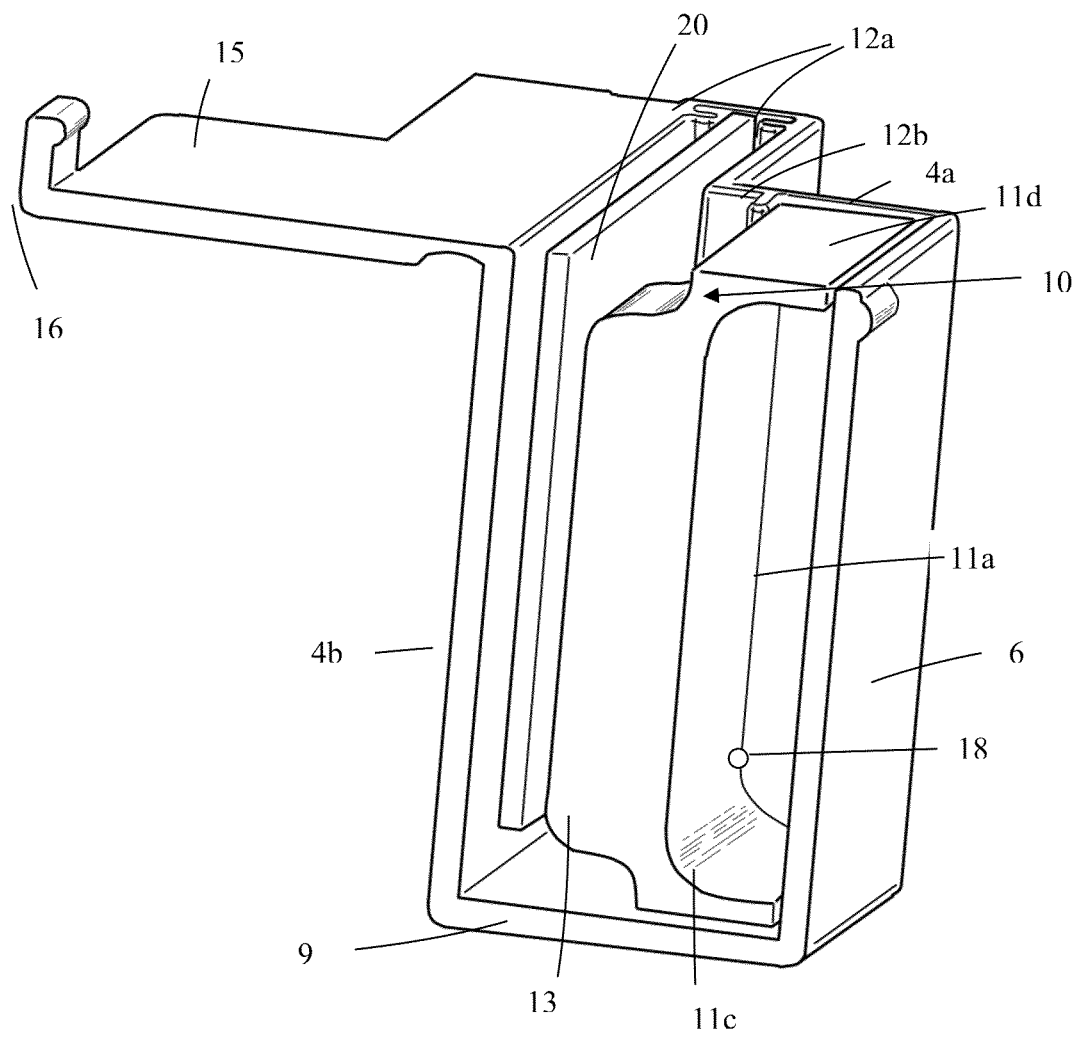
FIG. 6 is a cut-away isometric view of the inventive sheath at location A-A, showing a histology slide placed in the slide retainer and an empty sample block sleeve.

Sample block sleeve 10 comprises first sample block sleeve side wall 11a, second sample block sleeve side wall 11b, sample block sleeve bottom wall 11c, sample block sleeve top wall 11d, and sample block back wall 11e, as seen in FIG. 2. The sample block sleeve walls (11a through 11e) define sample storage space 18, which is substantially the same size as a paraffin block, as seen in FIG. 6.

Figure 5:
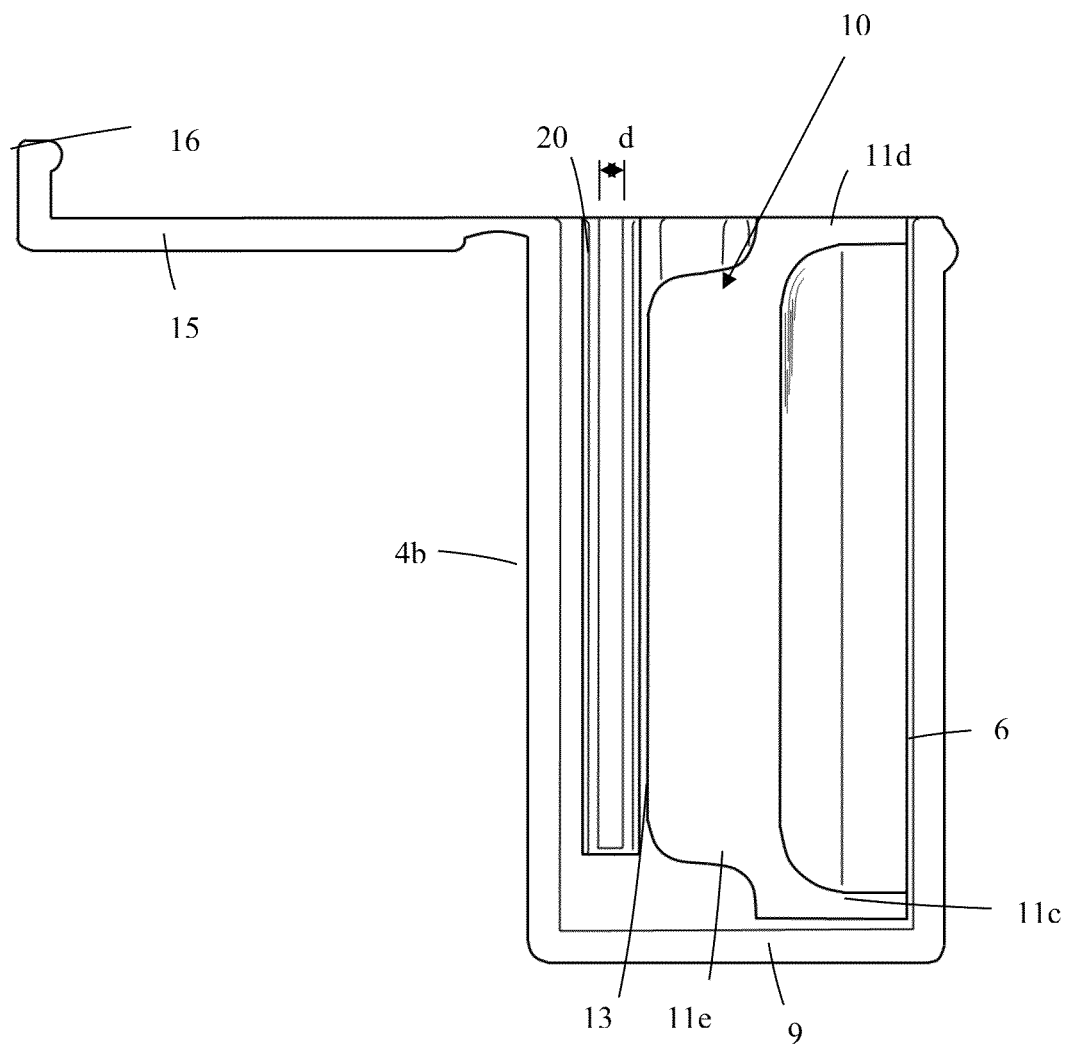
FIG. 5 is a cut-away side view of the inventive sheath at location A-A, showing a histology slide placed in the slide retainer and a sample block sleeve.

The sheath provides storage for both slide 20 and a paraffin block or other histology sample in sample block sleeve 10. Sample block sleeve projection 13 extends beyond sample block back wall 11e, as seen in FIGS. 3 and 5, and provides a surface for the user to grasp. Slide 20 and sample block sleeve 10 are separated by distance d to prevent damage to the slide, as seen in FIG. 5. It is noted that distance d may be modified by increasing the width of slide protective member 2, thereby further separating the slide from the sample block sleeve, or sample block sleeve projection 13 may be shrunk such that it extends less into slide protective member 2.

To store a sample, a paraffin tissue section is placed into sample block sleeve 10, after which sample block sleeve 10 is aligned with sample block sleeve retainers 12b and slid into sample block sleeve holder 5 such that sample block sleeve retainers 12b prevent sample block sleeve 10 from moving horizontally within sample block sleeve holder 5, as seen in FIG. 5. Pathology slide 20 is slid into slide storage 2 between a pair of slide retainers 12a, as seen in FIG. 3. Advantageously, sheath 1 secured the sample and slide in the inner space of the sheath and protects pathology slide 20 and the paraffin/sample block from damage. Further, the pathology slide may be accessed independently from the paraffin block, and vice versa. To access the slide, a user grasps the upper edge of the slide and pulls, advancing the slide along slide retainers 12a and out of sheath 1. To access the sample, a user grasps sample block sleeve 10 along sample block back wall 11e and above sample block sleeve projection 13 and pulls the sleeve upwards, along sample block sleeve retainers 12b and out of sheath 1.

Retrieval of sheath 1 from a storage location is accomplished using sheath retrieval lip 15. A user or automated system accesses a sample information index, which may be identifier 25, a storage catalogue index book, or other system known to those skilled in the art, and selects sheath retrieval lip 15 corresponding to the desired sheath. The user or automated system grasps the sheath retrieval lip or sheath retrieval clip and removes sheath 1 from storage. The sample and/or slide is accessed as discussed.

Example 2

Figure 7:
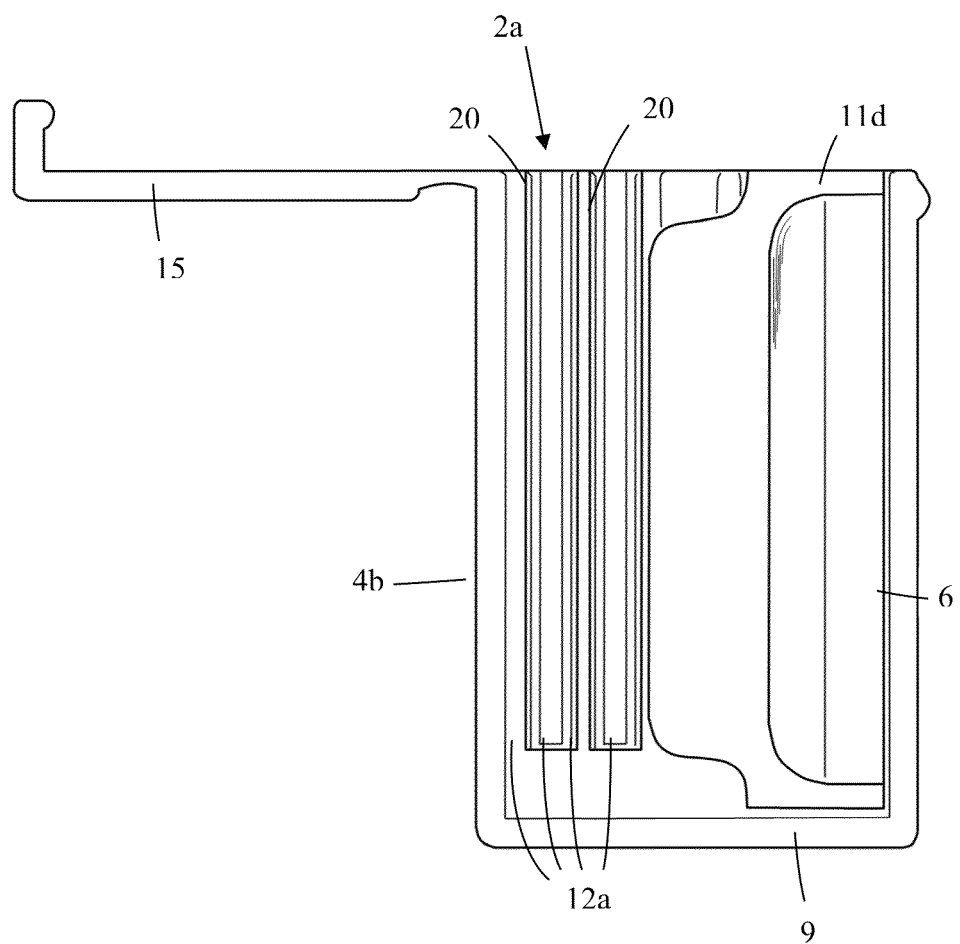
FIG. 7 is a cut-away side view of the inventive sheath at location A-A, showing an embodiment which accepts two histology slides placed parallel in the slide retainer and a sample block sleeve.

Sheath 1 comprises extended slide protective member 2a and histology sample protective member 5, as seen in FIG. 7. Extended slide protective member 2a has an exterior, as described in FIG. 1, with extended first vertical slide storage side wall 3a and second slide storage side wall 3b, such that two slides may be fitted within the interior space of slide protective member 2a, as seen in FIG. 7. A pair of slide retainers 12a are disposed on the interior face of vertical slide storage front wall 4a and vertical slide storage back wall 4b, as in Example 1. A second pair of slide retainers 12a are disposed in the interior space and are free standing, equidistant from the slide retainers disposed on the walls. Optionally, the face of the free standing slide retainers 12a that does not engage slide 20 is fused to the other free standing slide retainer, thereby forming a "|" shape, or the faces are fused to a support member forming a "+" shape. Alternatively, the slide retainers disposed in the interior space are fused to either first vertical slide storage side wall 3a or second slide storage side wall 3b for support. In this embodiment, a first slide may be placed between a first set of slide retainers 12a and a second slide may be placed parallel to the first slide in a second set of slide retainers 12a. The histology sample is stored in histology sample protective member 5, as described above. Access to the sheath, as well as each of the slides and the histology sample are as described in Example 1.

Example 3

Figure 8:
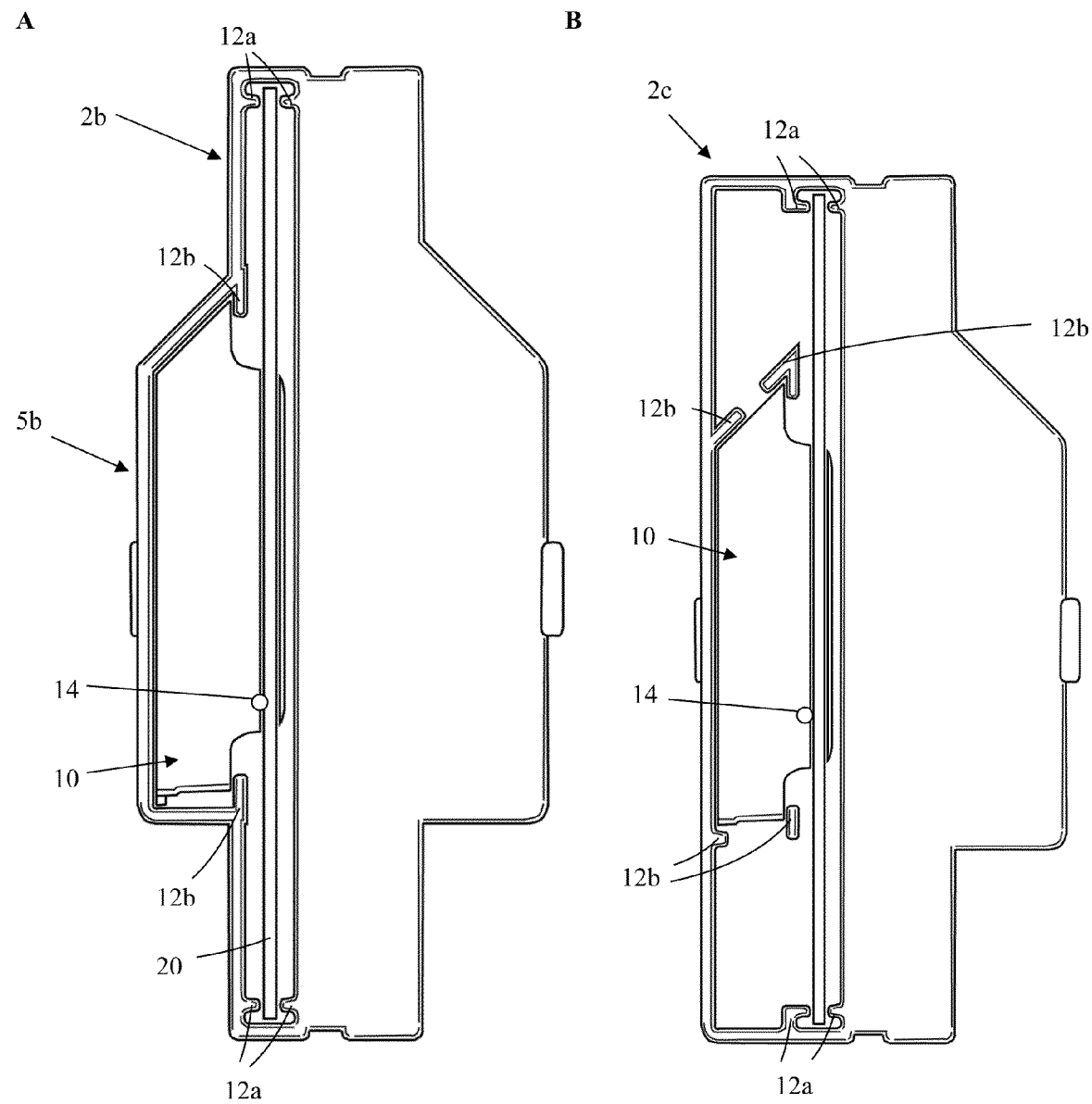
FIGS. 8(A) and (B) are top-down views of the inventive sheath, showing a histology slide placed in a slide opening of a sample block sleeve. (A) An embodiment of the invention with the histology sample protective member partially integrated into the slide protective member; and (B) an embodiment of the invention with the histology sample protective member completely integrated into the slide protective member, and the slide protective member extended to accept the sample block sleeve.
Figure 9:
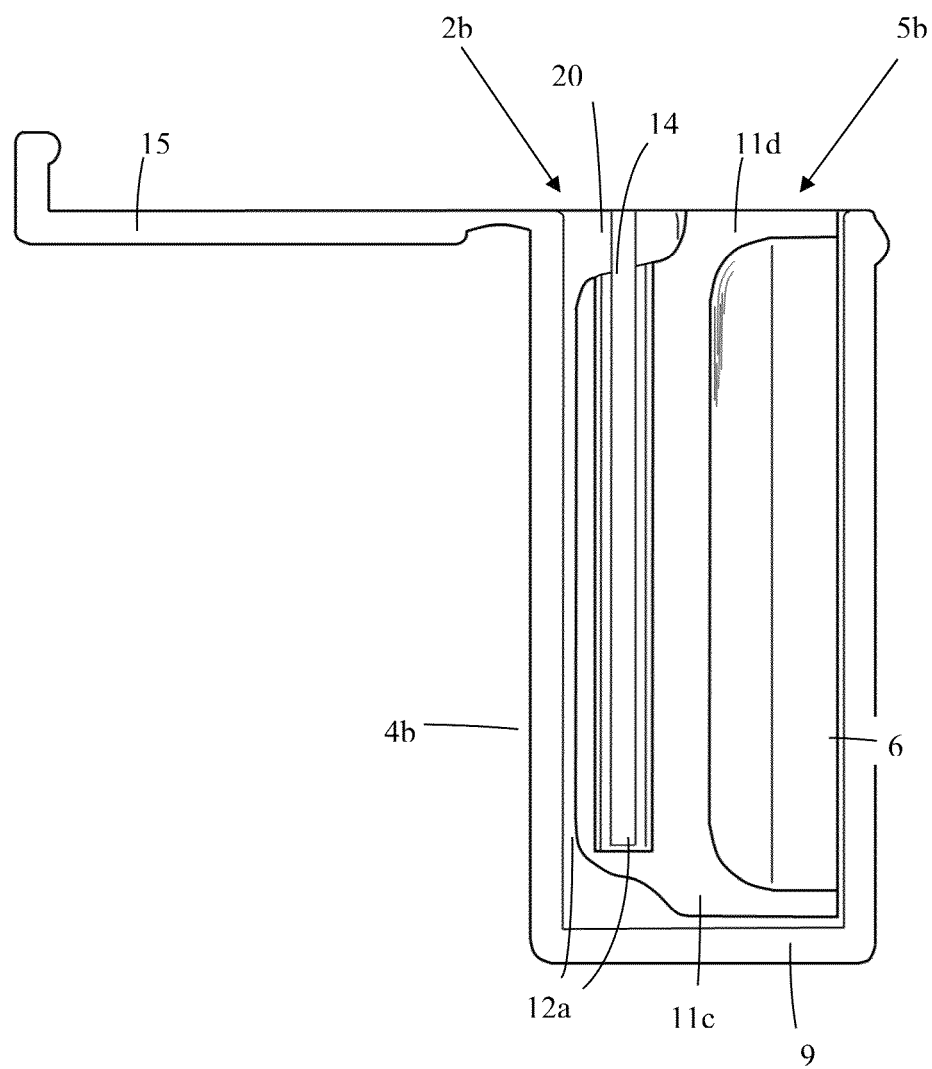
FIG. 9 is a cut-away side view of the inventive sheath at location A-A, showing a histology slide placed in a slide opening of a sample block sleeve.

Sheath 1 may be shrunken in width to reduce the amount of space required to store the histology samples and slides. Slide protective member 2 and histology sample protective member 5 are integrated together, with histology sample protective member 5 partially or fully integrated into slide protective member 2, as seen in FIGS. 8(A) and (B). For example, first vertical sample block sleeve side wall 7a and second vertical sample block sleeve side wall 7b of partially integrated histology sample protective member 5b are reduced in size, with sample block sleeve projection 13 extending into slide protective member 2b, as seen in FIGS. 8(A). Alternatively, slide protective member 2c is enlarged to accept both the slide and sample block sleeve 10, as seen in FIGS. 8(B). In either embodiment, the lower edge of sample block sleeve projection 13 is extended, as seen in FIG. 9, Slide opening 14 is disposed on the upper face of sample block sleeve projection 13, permitting slide 20 to extend through sample block sleeve projection 13.

Slide retainers 12a are integrated into the internal space in slide storage 2, adjacent to the corners of the inner space of slide protective member. Optionally, slide retainers 12a are protrusions on the walls of vertical slide storage front wall 4a and vertical slide storage back wall 4b. Alternatively, slide retainers 12a are disposed in slide opening 14, or two sets of slide retainers are used, a first set disposed adjacent to the corners of the inner space of slide protective member and a second set disposed in slide opening 14.

In this embodiment, the sample and histology slide cannot be accessed independently, as the slide must be removed before the paraffin sample or histology sample may be removed and accessed. However, the sheath compensates by requiring less storage space.

Example 4

Figure 10:
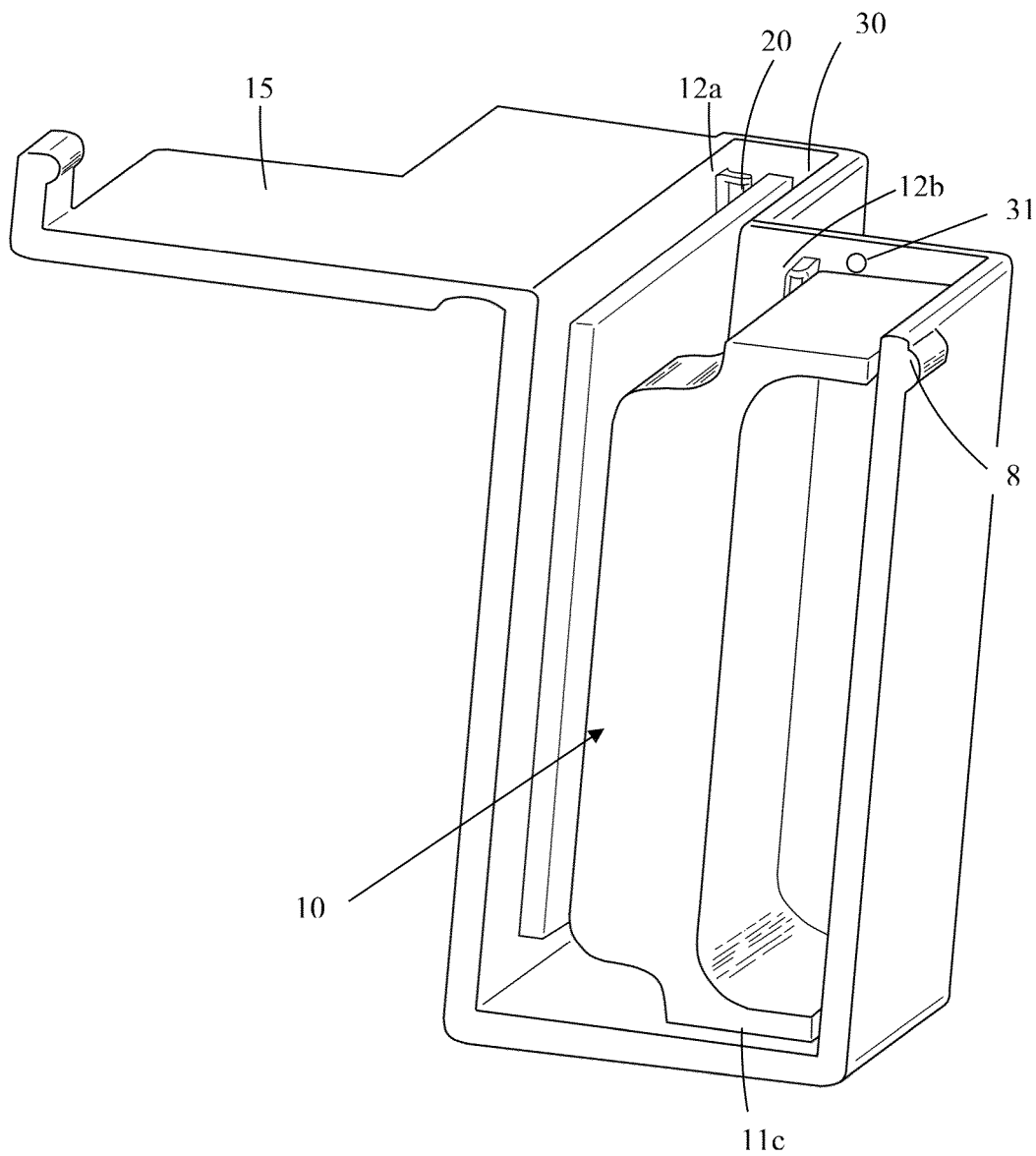
FIG. 10 is a cut-away isometric view of the inventive sheath at location A-A, showing the walls of the sheath extended. An optional lid is displayed which fits onto the elevated lip.

The vertical walls forming sheath 1, first vertical slide storage side wall 3a, second slide storage side wall 3b, vertical slide storage front wall 4a, vertical slide storage back wall 4b, first vertical sample block sleeve side wall 7a, second vertical sample block sleeve side wall 7b, vertical sample block sleeve front wall 6, are extended vertically forming elevated lip 30, as seen in FIG. 10. Slide 20, sample block sleeve 10, slide retainers 12a, and sample block sleeve retainers 12b are recessed into the interior space of sheath 1.

Elevated lip 30 provides protection to the slide from inadvertent damage to the upper surfaces of the slide. Optionally, friction lid 32a is dimensioned to fit within the interior space of sheath 1 and engage elevated lip 30 to form a protective cover. In some variations, textured or friction material 31 is disposed on the interior face of elevated lip 30 and provides a surface for friction lid 32a to tightly connect to. The friction connection may be used with any of the aforementioned Examples to provide a hard surface lid to protect the slide and histology sample. Advantageously, the lid also prevents the slide and histology sample from accidental loss, as the lid secures contents in the sheath.

Example 5

Figure 11:
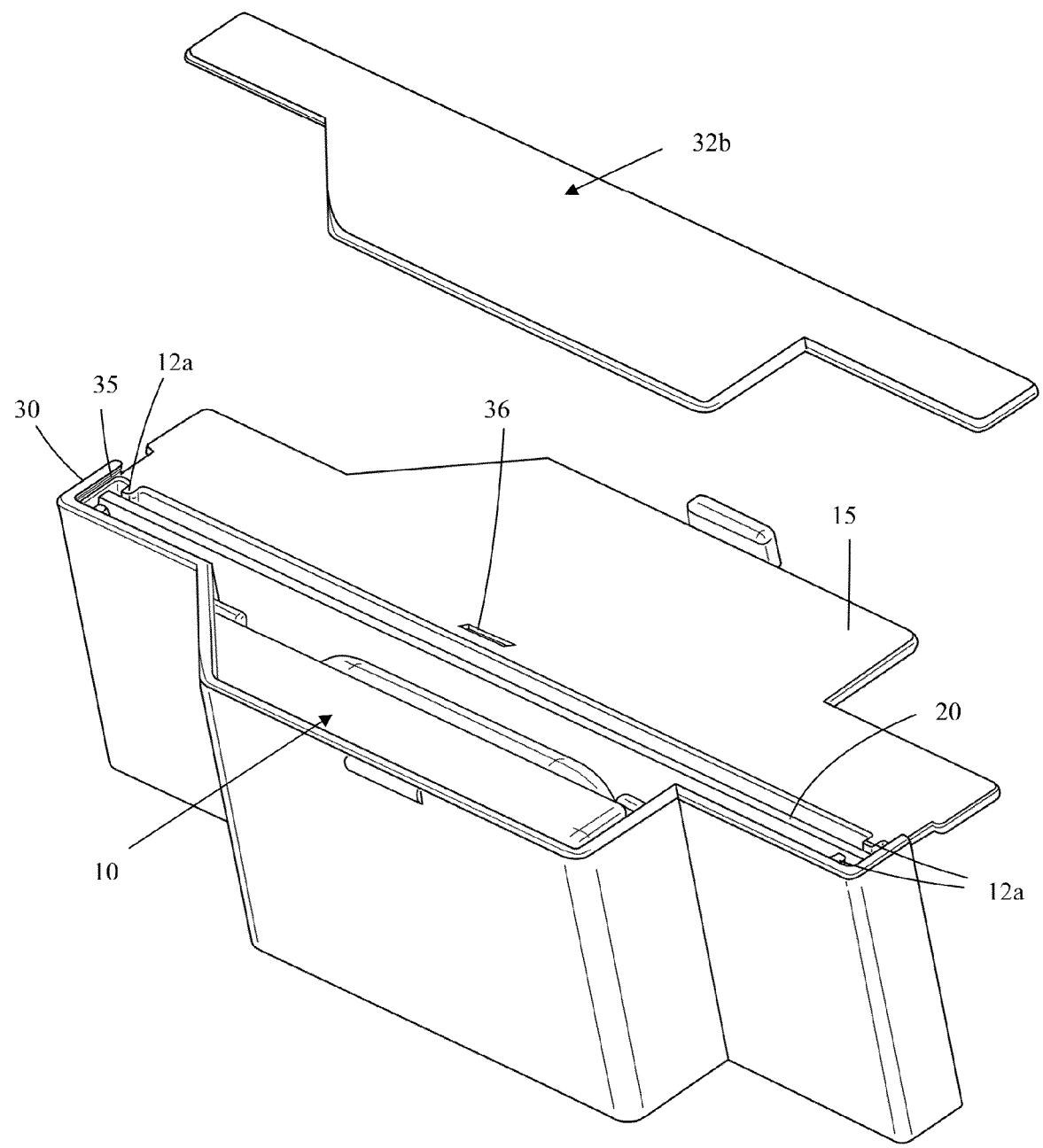
FIG. 11 is an isometric view of the inventive sheath, showing the front walls of the sheath extended and a lid channel integrated. A lid is displayed which fits into the lid channel providing a closable sheath.
Figure 12:
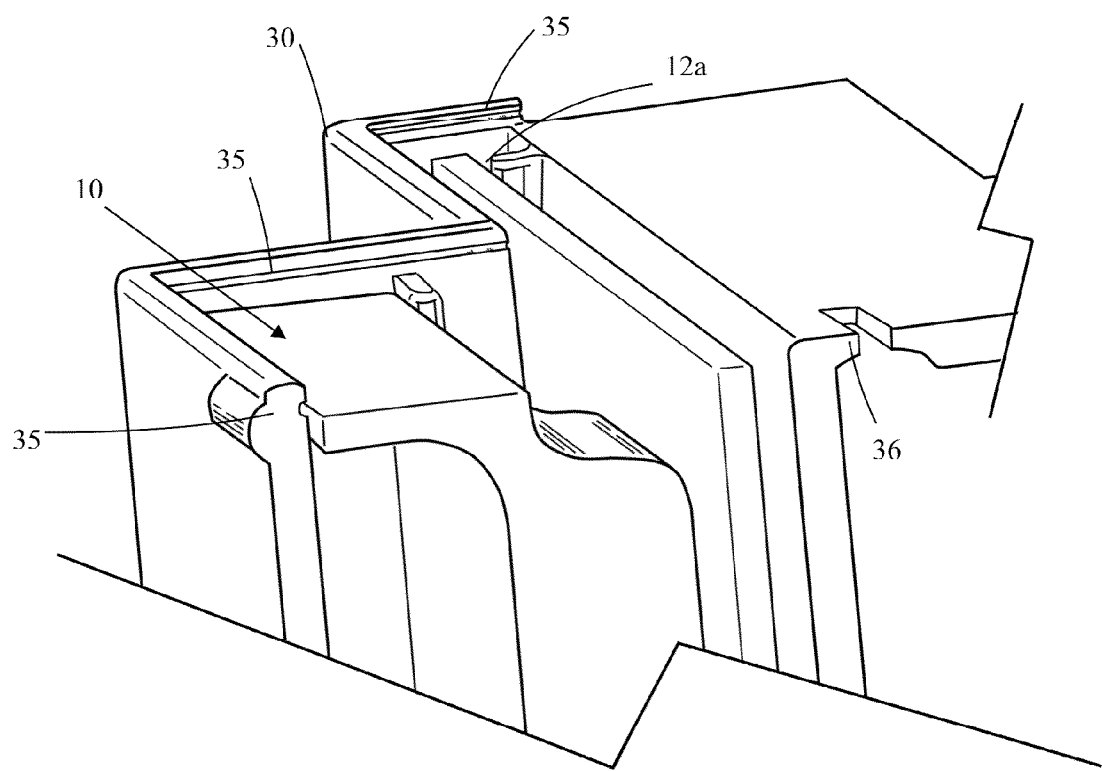
FIG. 12 is an enlarged, cut-away isometric view of the inventive sheath at location A-A, showing the front walls of the sheath extended and a lid channel integrated.

The contents of sheath 1 are secured using sliding lid 32b. The vertical walls forming sheath 1, first vertical slide storage side wall 3a, second slide storage side wall 3b, vertical slide storage front wall 4a, first vertical sample block sleeve side wall 7a, second vertical sample block sleeve side wall 7b, vertical sample block sleeve front wall 6, are extended vertically forming elevated lip 30, as seen in FIG. 11. Notably, in this example vertical slide storage back wall 4b is not elevated, and is level with slide 20, sample block sleeve 10, slide retainers 12a, and sample block sleeve retainers 12b. Lid channel 35 is disposed on the interior face of elevated lip 30, and runs along first vertical slide storage side wall 3a, second slide storage side wall 3b, vertical slide storage front wall 4a, first vertical sample block sleeve side wall 7a, second vertical sample block sleeve side wall 7b, vertical sample block sleeve front wall 6, as seen in FIG. 12.

Figure 13:
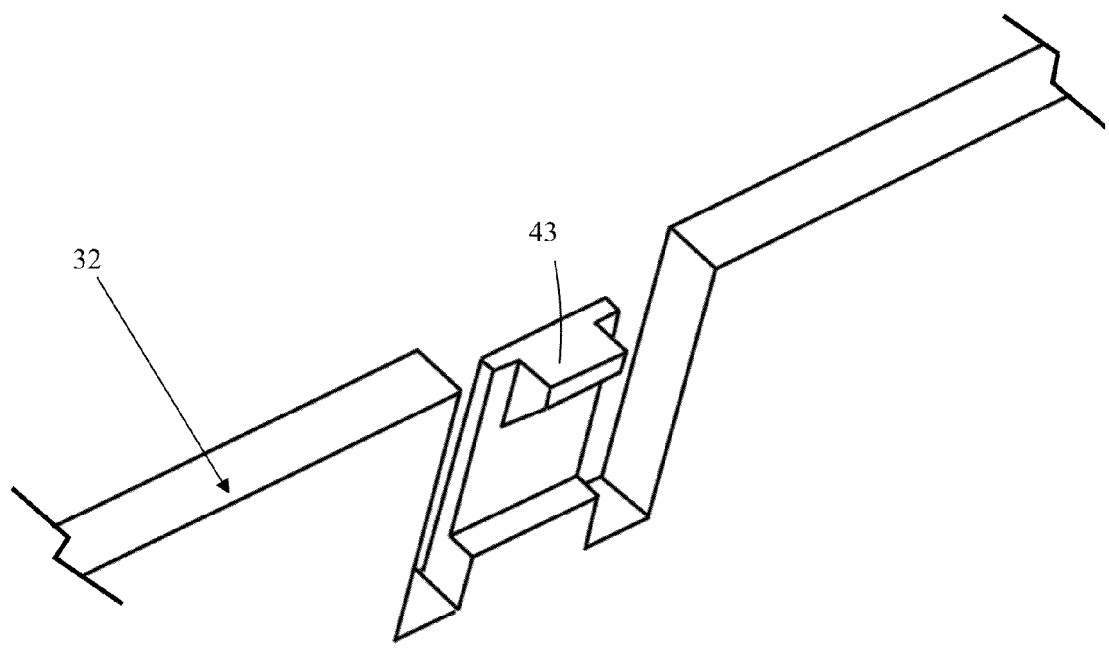
FIG. 13 is an enlarged, cut-away isometric view of a pressure loaded clip.

Sliding lid 32b is dimensioned to correspond to the shape of sheath 1, with the front edge adapted to fit in lid channel 35, thereby engaging elevated lip 30 to form a protective cover. Optionally, the back edge of sliding lid 32b includes a spring-loaded clip or pressure loaded clip as seen in FIG. 13, with lid lock groove 36 disposed on sheath retrieval lip 15 and adapted to engage the spring-loaded clip. In such embodiments, sliding lid 32b is placed into lid channel 35 and slid into the channel until the spring-loaded clip pushes down into lid lock groove 36. To remove the lid, a user presses down on the front edge of the spring-loaded clip, forcing the clip out of lid lock groove 36. The lid is then slid along lid channel 35 until the lid may be removed from the sheath.

Example 6

Figure 14:
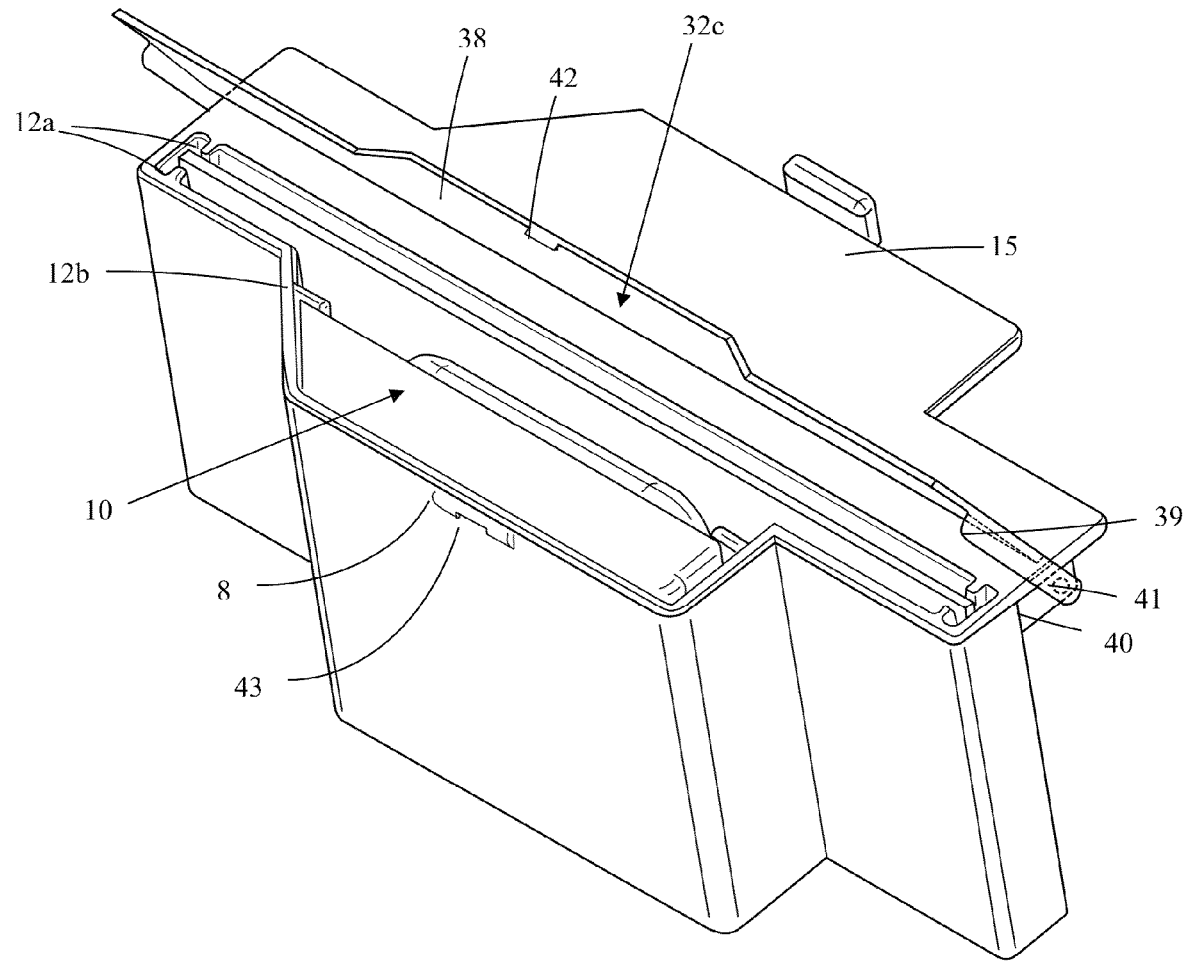
FIG. 14 is an isometric view of the inventive sheath, showing a pivoting lid.

The contents of sheath 1 are secured using pivoting lid 32c. Sheath 1 includes slide protective member 2 and histology sample protective member 5 as described in Example 1. Hinge projection 40 is disposed parallel to first vertical slide storage side wall 3a or second slide storage side wall 3b, and below sheath retrieval lip 15, as seen in FIG. 14. Hinge projection 40 includes hinge point 41.

Pivoting lid 32c includes lid face 38, which is dimensioned to correspond to the shape of sheath 1, with the front edge adapted to fit over protective member 2 and histology sample protective member 5 to form a protective cover. In some variations, lid face 38 also includes a lip which firmly fits over the edge of vertical walls forming sheath 1, first vertical slide storage side wall 3a, second slide storage side wall 3b, vertical slide storage front wall 4a, first vertical sample block sleeve side wall 7a, second vertical sample block sleeve side wall 7b, vertical sample block sleeve front wall 6, such that pivoting lid 32c firmly fits over slide protective member 2 and histology sample protective member 5. Lid hinge 39 is perpendicular to lid face 38 and disposed on each of the side edges of pivoting lid 32c. Adjacent to the back edge of lid hinge 39 lid hinge 39, lid hinge 39 includes a pivot point which is dimensioned to engage hinge point 41, thereby permitting pivoting lid 32c to pivot on hinge point 41 and facilitating opening and closing of pivoting lid 32c. Optionally, the front edge of pivoting lid 32c includes a spring-loaded clip 42 or pressure loaded clip 43, such as the one depicted in FIG. 13. The clip may engage the front face of vertical sample block sleeve front wall 6 or sample protection member projection 8. Where sample protection member projection 8 is used to secure pivoting lid 32c, it is advantageous for sample protection member projection 8 to include clip lock 43 on the lower edge of sample protection member projection 8, as seen in FIG. 14. Clip lock 43 provides an opening to accept the clip thereby securing pivoting lid 32c to sheath 1.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a dual histology sample and slide storage system, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A protective sheath, comprising:
    a histology slide protective member, further comprising:
        four vertical walls disposed in communication with a lower horizontal wall, wherein the walls define an open-faced box, wherein the walls define an internal space, where the interior space is dimensioned to accept at least one histology slide;
        a plurality of ridges disposed on the interior horizontal walls and adapted to accept the histology slide;
    a histology sample protective member in permanent communication with the histology slide, further comprising:
        a sample block sleeve holder disposed on a first vertical wall of the histology slide protective member and adapted to accept a paraffin block cassette, wherein the sample block sleeve holder further comprises:
            a first sample member vertical wall and third sample member vertical wall in communication with the first vertical wall of the histology slide protective member;
            a second sample member vertical wall in communication with the first sample member vertical wall and third sample member vertical wall;
            a sample member horizontal wall;
            wherein the sample member vertical walls and horizontal wall define an interstitial space; and
        a sample block sleeve having three vertical sample block sleeve walls disposed in communication with an upper horizontal sample block sleeve wall and a lower horizontal sample block sleeve wall, wherein the walls define an internal paraffin block space;
        wherein the internal sample block space is adapted to accept a sample or paraffin block.

2. The protective sheath of claim 1, further comprising a horizontal retrieval lip disposed on the upper edge of a second vertical wall of the histology slide protective member.

3. The protective sheath of claim 2, further comprising a retrieval clip disposed on the retrieval lip.

4. The protective sheath of claim 1, wherein the sheath is constructed of plastic.

5. The protective sheath of claim 1, wherein the sheath is constructed of polyethylene, polypropylene, polyethylene terephthalate, polyvinylchloride, polyvinylidenechloride, polycarbonate, polyurethane, polyamide, polytetrafluoroethylene, polyvinylacetate, wood, ceramic, cardboard, fiberboard, titanium, stainless steel, or surgical steel.

6. The protective sheath of claim 1, wherein the horizontal wall of the histology slide protective member and the horizontal wall of the histology sample protective member integrated into one horizontal wall.

7. The protective sheath of claim 1, further comprising a plurality of ridges disposed on the interior horizontal walls of the first sample member vertical wall and third sample member vertical wall and adapted to accept the sample block sleeve.

8. The protective sheath of claim 1, further comprising:
    four ridges disposed on the interior horizontal walls and adapted to accept the histology slide; or
    eight ridges, wherein four ridges are disposed on the interior horizontal walls of the histology slide protective member forming a first set of slide ridges and a second set of slide ridges, and wherein two ridges are disposed between the first set of slide ridges and two ridges are disposed between the second set of slide ridges, such that the eight ridges are adapted to accept two histology slides in the histology slide member.

9. The protective sheath of claim 1, further comprising a retention system, wherein the retention system comprises
    a pivoting lid, further comprising:
        a lid face dimensioned to cover the upper edge of the histology slide protective member and histology sample protective member;
        a plurality of lid hinge faces disposed perpendicular to the lid face, and adapted to hingedly engage a plurality of hinge point disposed on a plurality of hinge projections, or a hinge point disposed on a second vertical wall of the histology slide protective member and a third vertical wall of the histology slide protective member;
            where the hinge projection is disposed adjacent to and parallel the second vertical wall of the histology slide protective member and the third vertical wall of the histology slide protective member
    a slidingly connected lid, further comprising:
        at least one channel disposed on the interior face of the first vertical wall of the histology slide protective member, the second vertical wall of the histology slide protective member, the third vertical wall of the histology slide protective member, the first sample member vertical wall, the second sample member vertical wall, and the third sample member vertical wall in communication with the first vertical wall of the histology slide protective member;
        a sliding lid adapted to engage the channel and dimensioned to cover the upper edge of the histology slide protective member and histology sample protective member;
    a pressure-fitted lid, further comprising:
        an elevated lip, wherein the first vertical wall of the histology slide protective member, the second vertical wall of the histology slide protective member, the third vertical wall of the histology slide protective member, fourth vertical wall of the histology slide protective member, the first sample member vertical wall, the second sample member vertical wall, and the third sample member vertical wall in communication with the first vertical wall of the histology slide protective member are elongated to form the elevated lip; and
    a friction lid, wherein the friction lid is adapted to frictionly engage the interior space of the elevated lip.

10. The protective sheath of claim 9, further comprising an elevated lip on the slidingly connected lid;
    wherein the wherein the first vertical wall of the histology slide protective member, the second vertical wall of the histology slide protective member, the third vertical wall of the histology slide protective member, the first sample member vertical wall, the second sample member vertical wall, and the third sample member vertical wall in communication with the first vertical wall of the histology slide protective member are elongated to form the elevated lip.

11. The protective sheath of claim 9, further comprising a spring-loaded clip or pressure loaded clip;
  wherein the a spring-loaded clip or pressure loaded clip is disposed on the back edge of the sliding lid; and
  a lid lock groove disposed on a sheath retrieval lip and adapted to engage the spring-loaded clip, wherein the sheath retrieval lip is disposed on the upper edge of a second vertical wall of the histology slide protective member.

12. The protective sheath of claim 9, further comprising a lip on the pivoting lid;
  wherein lid face of the pivoting lid further comprises a first front sample block sleeve edge, a second side sample block edge, a third side sample block edge, a first front slide storage edge, a second side slide storage edge, a third side slide storage edge, and a fourth back slide storage edge;
  wherein the plurality of lid hinge faces are disposed on the second side slide storage edge and the third side slide storage edge; and
  wherein the lip is disposed on the first front sample block sleeve edge, the second side sample block edge, the third side sample block edge, the first front slide storage edge, the second side slide storage edge, and the third side slide storage edge.

13. The protective sheath of claim 12, further comprising a spring-loaded clip or pressure loaded clip disposed on the lip, wherein the spring-loaded clip or pressure loaded clip is disposed on the first front sample block sleeve edge; and
  a clip lock disposed on the face of the first sample member vertical wall, and wherein the clip lock is adapted to accept the spring-loaded clip or pressure loaded clip.

14. The protective sheath of claim 9, further comprising a textured or friction material disposed on the interior face of elevated lip, wherein the textured or friction material is adapted to engage the pressure-fitted lid.

15. The protective sheath of claim 1, further comprising a coating on the edges of the at least one opening adapted to accept a tissue slide, wherein the coating is Teflon, polyester, para-phenylenediamine, terephthaloyl chloride polymer, carbon fiber, expanded PTFE, meta-phenylenediamine, nylon, polypropylene, latex, silicone, polyurethane, polyisoprene polyvinylchloride, ethylene propylene diene monomer, styrene, cornstarch powder, graphite, meta-aramid compounds, or para-aramid compounds.

* * * * *